(12) United States Patent
Fukasawa et al.

(10) Patent No.: US 9,200,263 B2
(45) Date of Patent: Dec. 1, 2015

(54) RECOMBINANT PRPK-TPRKB AND USES THEREOF

(71) Applicant: TAIHO PHARMACEUTICAL CO., LTD., Chiyoda-ku (JP)

(72) Inventors: Kazuhiro Fukasawa, Tsukuba (JP); Keisuke Ishida, Hanno (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 14/365,021

(22) PCT Filed: Dec. 14, 2012

(86) PCT No.: PCT/JP2012/083169
§ 371 (c)(1),
(2) Date: Jun. 12, 2014

(87) PCT Pub. No.: WO2013/089278
PCT Pub. Date: Jun. 20, 2013

(65) Prior Publication Data
US 2015/0004645 A1 Jan. 1, 2015

Related U.S. Application Data

(60) Provisional application No. 61/570,420, filed on Dec. 14, 2011.

(51) Int. Cl.
*C12N 9/12* (2006.01)
*C07K 14/47* (2006.01)

(52) U.S. Cl.
CPC .............. *C12N 9/12* (2013.01); *C07K 14/4703* (2013.01); *C12Y 207/11001* (2013.01)

(58) Field of Classification Search
None
See application file for complete search history.

(56) References Cited

U.S. PATENT DOCUMENTS

| 2006/0211728 A1 | 9/2006 | Greig et al. |
| 2007/0134261 A1 | 6/2007 | Hancock et al. |
| 2007/0208057 A1 | 9/2007 | Zeldis |
| 2011/0319277 A1* | 12/2011 | Park et al. ................. 506/7 |

OTHER PUBLICATIONS

Kotoshiba et al., Molecular Dissection of the Interaction between p27 and Kip1 Ubiquitylation-promoting Complex, the Ubiquitin Ligase That Regulates Proteolysis of p27 in G1 Phase; JBC, vol. 280, No. 18, pp. 17694-17700, 2005.*
International Search Report issued Mar. 21, 2013, in PCT/JP12/083169 filed Dec. 14, 2012.
Written Opinion of the International Searching Authority issued Mar. 21, 2013, in PCT/JP12/083169 filed Dec. 14, 2012.
International Search Report issued Apr. 9, 2012, in PCT/US11/40918 filed Jun. 17, 2011.
Written Opinion of the International Searching Authority issued Apr. 9, 2012, in PCT/US11/40918 filed Jun. 17, 2011.
Miyoshi, et al., "Identification of CGI-121, a novel PRPK (p53-related protein kinase)-binding protein", Biochemical and Biophysical Research Communications, vol. 303, No. 2, XP002693257, Apr. 2003, pp. 399-405.
Schmid, et al., "Advantage of a baculovirus expression system for protein-protein inter-action studies. Involvement of posttranslational phosphorylation in the interaction between wt p53 protein and poly(ADP-ribose) polymerase-1", Acta Biochimca Polonica, XP-002693258, vol. 52, No. 3, 2005, pp. 713-719.
Costessi, et al., "The Human EKC/KEOPS Complex is Recruited to Cullin2 Ubiquitin Ligases by the Human Tumour Antigen PRAME", PLOS ONE, vol. 7, No. 8, E42822, Aug. 2012, XP002693259, pp. 1-13.
Ito, et al., Identification of a Primary Target of Thalidomide Teratogenicity, Science vol. 327, Mar. 2010, 7 pages.
"Haematologica", the hematology journal, 13 th International Myeloma Workshop, May 2011, 2 pages.
Abe, et al., "A Small Ras-like protein Ray/Rab1c modulates the p53-regulating activity of PRPK", Biochemical and Biophysical Research Communications, vol. 344, 2006, pp. 377-385.
Haslett, et al., "Thalidomide Stimulates T Cell Responses and Interleukin 12 Production in HIV-Infected Patients", AIDS Research and Human Retroviruses, vol. 15, No. 13, 1999, pp. 1169-1179.
Manning, et al., "The Protein Kinase Complement of the Human Genome", Science 2002, vol. 298, Dec. 2002, 7 pages.
Mao, et al., "Atomic structure of the KEOPS complex: an ancient protein kinase-containing molecular machine", Mol Cell, 32(2), Oct. 24, 2008, 25 pages.
Abe, et al., "Cloning and Characterization of a p53-related Protein Kinase Expressed in Interleukin-2 activated Cytotoxic T-cells, Epithelial Tumor Cell Lines, and the Testes", The Journal of Biological Chemistry, vol. 276, No. 47, 2001, pp. 44003-44011.
Kuprash, et al., Ablation of TNF or lymphotoxin signaling and the frequency of spontaneous tumors in p53-deficient mice, Cancer Letters, vol. 268, 2008, pp. 70-75.
Farina, et al., "Investigating the KEOPS/EKC complex function in *C. elegans*.", International Worm Meeting, http://www.citeulike.org/group/6190/article/3333461, Oct. 3, 2011, 2 pages.

(Continued)

*Primary Examiner* — Jennifer Dunston
*Assistant Examiner* — Addison D Ault
(74) *Attorney, Agent, or Firm* — Oblon, McClelland, Maier & Neustadt, L.L.P.

(57) ABSTRACT

The present invention provides a recombinant PRPK protein, a recombinant TPRKB protein, or a recombinant PRPK/TPRKB complex expressed by use of a eukaryotic cell expression system. The present invention also provides a method of preparing a recombinant PRPK, a recombinant TPRKB, or a recombinant PRPK/TPRKB, comprising expressing a recombinant PRPK, a recombinant TPRKB, or a recombinant PRPK/TPRKB complex by use of a eukaryotic cell expression system. The present invention also provides a method of identifying an agent that modulates PRPK, TPRKB, or PRPK/TPRKB complex using the recombinant PRPK, the recombinant PRPK or the recombinant PRPK/TPRKB complex.

6 Claims, 3 Drawing Sheets

(56) References Cited

OTHER PUBLICATIONS

Downey, et al., "A Genome-Wide Screen Identifies the Evolutionarily Conserved KEOPS Complex as a Telomere Regulator", Cell 124, Mar. 24, 2006, pp. 1155-1168.

Facchin, et al., "Functional homology between yeast piD261/Bud32 and human PRPK: both phosphorylate p53 and PRPK partially complements piD261/Bud32 deficiency", FEBS Letters 549, 2003, pp. 63-66.

Vandermeeren, et al., "Subcellular forms and biochemical events triggered in human cells by HCV polyprotein expression from a viral vector", Virology Journal, 2008, 20 pages.

Fifth Canadian Symposium on Telomeres and Telomerase, May 11-14, 2006, 74 pages.

Peterson, et al., A Chemosensitization Screen Identifies TP53RK, a Kinase that Restrains Apoptosis after Mitotic Stress, Cancer Research, 70(15), Aug. 2010, 12 pages.

\* cited by examiner

RECOMBINANT PRPK-TPRKB AND USES THEREOF

CROSS REFERENCE TO RELATED APPLICATION

This application is a National Stage of PCT/JP12/083169 filed Dec. 14, 2012 and claims priority from U.S. Provisional Patent Application No. 61/570,420 filed on Dec. 14, 2011, which is incorporated herein by reference in its entirety.

TECHNICAL FIELD OF THE INVENTION

The present invention is related to a recombinant PRPK protein, a recombinant TPRKB protein and a recombinant PRPK/TPRKB complex expressed by use of a eukaryotic cell expression system.

BACKGROUND OF THE INVENTION

Lenalidomide (Revlimid®, made by Celgene Corporation) is an orally available thalidomide analog and has been approved by the U.S. Food and Drug Administration for use in patients with multiple myeloma and myelodysplastic syndromes. In 2009, sales of Revlimid® reached USD $ 1.7 billion and sales in 2010 are expected to exceed USD $2.0 billion, making Revlimid® one of the most successful oncology products introduced into commerce in the past five years.

Lenalidomide has direct anti-tumor effect, inhibition of the microenvironment support for tumor cells, and immunomodulatory role and exerts anti-angiogenic and immunomodulatory/anti-inflammatory properties. However, Revlimid® is sold under an FDA mandated risk mitigation program with a 'Black Box Warning' describing the risks of birth defects because of thalidomide's well-known teratogenic effects. The protein target responsible for the teratogenicity of thalidomide was published as Cereblon (Ito et al, Science 327:1345-1350 (2010), Y. X. Zhu et al, $13^{th}$ International Myeloma Workshop O-05 (2011)); however, the anticancer target(s) of Immunomodulatory drugs (IMiD's) are still unknown.

PRPK and TPRKB, are evolutionarily conserved from archaea and yeast to humans; yet very little is known about the function of these proteins, especially in humans. In yeast and archaea, Bud32 and Cgi121 (PRPK and TPRKB, respectively) have previously been demonstrated to form a functional complex named KEOPS with two other proteins called Kae1 and Pcc1. The yeast KEOPS complex is required for telomere maintenance and transcriptional regulation. The structure of the KEOPS complex has been studied by crystallography, although the proteins were of mixed origin (mostly archaea). Structure-based sequence alignments indicate that Bud32 (PRPK) is an atypical kinase that possesses an architecture characteristic of protein kinases but lacks an activation loop that is normally responsible for substrate recognition. PRPK and TPRKB are co-expressed in human cell line. PRPK and TPRKB are proteins relating to p53 in human. PRPK is TP53-regulating kinase protein and TPRKB is p53-related protein kinase-binding protein. However, formation and biological function of the human KEOPS complex has not been reported.

SUMMARY OF THE INVENTION

In one embodiment, the present invention provides a method of preparing a recombinant PRPK, a recombinant TPRKB, a recombinant PRPK/TPRKB complex, or a homolog thereof wherein the method comprises expressing a recombinant PRPK, a recombinant TPRKB, a recombinant PRPK/TPRKB complex, or a homolog thereof by use of a eukaryotic cell expression system. The present invention also provides a recombinant PRPK protein, a recombinant TPRKB protein, a recombinant PRPK/TPRKB complex, or a homolog thereof expressed by use of a eukaryotic cell expression system. In one embodiment, the recombinant PRPK protein, the recombinant TPRKB protein, the recombinant PRPK/TPRKB complex, or the homolog thereof are isolated with a purity of 90% or more.

In another embodiment, the present invention provides a method of identifying an agent that interacts with (e.g., modulates) PRPK/TPRKB complex or homolog thereof. The method comprises: providing a system comprising a PRPK or a homolog thereof and a TPRKB or a homolog thereof, wherein the PRPK, the TPRKB or the homolog thereof are recombinant proteins expressed by a eukaryotic cell expression system; providing a test agent; contacting the test agent with the system; and detecting an interaction between the test agent and at least one of the recombinant PRPK or the homolog thereof and the recombinant TPRKB or the homolog thereof.

In yet another embodiment, the present invention provides a method of identifying an agent that interacts with (e.g., modulates) PRPK (also known as TP53RK), TPRKB or homolog thereof. The method comprises: providing a system comprising a PRPK, a TPRKB or a homolog thereof, wherein the PRPK, the TPRKB and the homolog thereof are recombinant proteins expressed by a eukaryotic cell expression system; providing a test agent; contacting the test agent with the system; and detecting an interaction between the test agent and the recombinant PRPK, the recombinant TPRKB or the recombinant homolog thereof.

In some embodiments, any such methods of identifying an agent comprise providing a plurality of test agents. In some embodiments, two or more test agent members of the plurality of test agents share at least one common structural element or moiety. In some embodiments, two or more test agent members of the plurality of test agents share a core structure element. The present invention also provides agents, modulators, reagents, compounds and compositions identified with the recombinant.

In preferred embodiment of the invention, the eukaryotic cell expression system is baculovirus-insect cell expression system.

In further embodiment, the present invention provides a baculovirus vector, wherein a polynucleotide encoding at least one of PRPK, TPRKB, PRPK/TPRKB complex and homolog thereof is incorporated therein. The present invention also provides a cultured insect cell comprising the baculovirus vector. The present invention also provides a baculovirus-insect cell expression system comprising the cultured insect cell.

This application refers to various patent publications, all of which are entirely incorporated herein by reference.

DETAILED DESCRIPTION OF THE INVENTION

Figure 1:
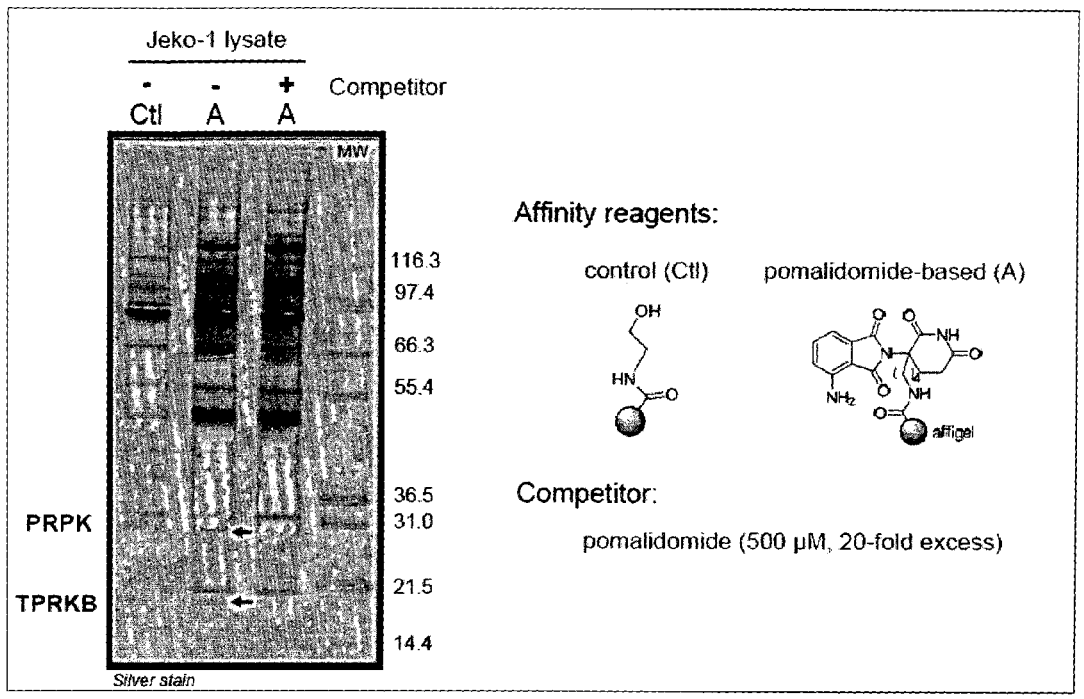
FIG. 1. PRPK and TPRKB captured with pomalidomide-based affinity reagent. PRPK and TPRKB were only captured from sensitive cell line (Jeko-1); PRPK and TPRKB were not captured from HeLa S3 cells.

Recently, it was discovered that lenalidomide and its analogs interact with a PRPK/TPRKB complex and affect their activities. PRPK and TPRKB are promising tools for Drug Discovery Research. However, this technique suffers from the difficulty to obtain enough amounts of purified PRPK and TPRKB proteins to establish high throughput drug screening system since expression of these proteins are only transient.

It has been reported that PRPK and TPRKB proteins were transiently co-expressed in human cell line. The trangent cell expression system may be available for identifying an agent that modulates PRPK, TPRKB, or PRPK/TPRKB complex. This system, however, provides undesired identified agent because the agent can bind to PRPK, TPRKB, or PRPK/TPRKB complex indirectly via impure ingredient from the cells due to reduction of the expression. It is also a problem that trangent cell expression system is not capable of providing enough amount of the proteins or their complex for efficient screening of agents that modulate PRPK, TPRKB, or PRPK/TPRKB complex. Stable cell expression system is, therefore, preferable.

The inventors have discovered that recombinant of PRPK, TPRKB, PRPK/TPRKB complex or homolog thereof is stably expressed at high yield and high purity by using a eukaryotic cell expression system such as baculovirus-insect cell expression system and found that the recombinant of PRPK, TPRKB, PRPK/TPRKB complex or homolog thereof expressed by the eukaryotic cell expression system is useful in identifying a compound that interacts with PRPK, TPRKB, homolog thereof, PRPK/TPRKB complex or homolog thereof, i.e., a candidate of lenalidomide analog. The recombinants expressed by the eukaryotic cell expression system enable the methods of identifying an agent, the screening methods, and the detecting steps according to the present invention to be conducted efficiently and accurately.

Accordingly, in one embodiment, the present invention provides a method of preparing a recombinant PRPK, a recombinant TPRKB, a recombinant PRPK/TPRKB complex, or a homolog thereof, wherein the method comprises expressing a recombinant PRPK, a recombinant TPRKB, a recombinant PRPK/TPRKB complex or a recombinant homolog thereof by use of a eukaryotic cell expression system. The present invention also provides a recombinant PRPK protein, a recombinant TPRKB protein, a recombinant PRPK/TPRKB complex or a recombinant homolog thereof expressed by use of a eukaryotic cell expression system.

In another embodiment, the present invention provides a method of identifying an agent that interacts with (e.g., modulates) PRPK/TPRKB complex or homolog thereof. The method comprises: providing a system comprising a PRPK or a homolog thereof and a TPRKB or a homolog thereof, wherein the PRPK or the homolog thereof and the TPRKB or the homolog thereof are recombinant proteins expressed by a eukaryotic cell expression system; providing a test agent; contacting the test agent with the system; and detecting an interaction between the test agent and at least one of the recombinant PRPK or the homolog thereof and the recombinant TPRKB or the homolog thereof.

In yet another embodiment, the present invention provides a method of identifying an agent that interacts with (e.g., modulates) PRPK (also known as TP53RK), TPRKB or homolog thereof. The method comprises: providing a system comprising a PRPK, a TPRKB or a homolog thereof, wherein the PRPK, the TPRKB and the homolog thereof are recombinant proteins expressed by a eukaryotic cell expression system; providing a test agent; contacting the test agent with the system; and detecting an interaction between the test agent and the recombinant PRPK, the recombinant TPRKB or the recombinant homolog thereof.

DEFINITIONS

Amino acid: As used herein, the term "amino acid," in its broadest sense, refers to any compound and/or substance that can be incorporated into a polypeptide chain. In some embodiments, an amino acid has the general structure H2N—C(H)(R)—COOH. In some embodiments, an amino acid is a naturally-occurring amino acid. In some embodiments, an amino acid is a synthetic or un-natural amino acid; in some embodiments, an amino acid is a D-amino acid (e.g., α,α-disubstituted amino acids, N-alkyl amino acids, lactic acid); in some embodiments, an amino acid is an L-amino acid. "Standard amino acid" refers to any of the twenty standard L-amino acids commonly found in naturally occurring peptides. "Nonstandard or unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to salts, amino acid derivatives (such as amides), and/or substitutions. Amino acids, including carboxy- and/or aminoterminal amino acids in peptides, can be modified by methylation, amidation, acetylation, and/or substitution with other chemical groups that can change the peptide's circulating halflife without adversely affecting its activity. Examples of unconventional or un-natural amino acids include, but are not limited to, citrulline, ornithine, norvaline, 4-(E)-butenyl-4(R)-methyl-N-methylthreonine (MeBmt), N-methyl-leucine (MeLeu), aminoisobutyric acid, statine, and N-methyl-alanine (MeAla). Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" or "characteristic portion of an antibody" are used interchangeably and refer to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids.

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, and/or 3' end formation); (3) translation of an RNA into a polypeptide or protein; (4) post-translational modification of a polypeptide or protein.

Host cell: As used herein, the "host cell" is a cell that is manipulated according to the present disclosure. A "modified host cell", as used herein, is any host cell which has been modified, engineered, or manipulated in accordance with the present disclosure as compared with an otherwise identical parental cell, and/or as compared with a particular reference cell (e.g., a wild type cell).

Introduce: The term "introduce", as used herein with reference to introduction of a nucleic acid into a cell or organism is intended to have its broadest meaning and to encompass introduction, for example by transformation methods (e.g., calcium-chloridePage mediated transformation, electroporation, particle bombardment), and also introduction by other methods including transduction, conjugation, and mating. In some embodiments, a vector is utilized to introduce a nucleic acid into a cell or organism.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism such as a non-human animal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Modified: The term "modified" may be used herein to refer to an entity (e.g., a cell or organism) that has been manipulated by the hand of man. For example, in some embodiments, a modification may be or comprise any chemical, physiological, genetic, or other modification that appropriately alters characteristics of a host organism as compared with an otherwise identical reference organism not subjected to the modification. In most embodiments, a modification will comprise a genetic modification. In some embodiments, a modification comprises at least one chemical, physiological, genetic, or other modification; in some embodiments, a modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Modulator: As used herein, the term "modulator" typically refers to a compound that alters or elicits an activity. For example, the presence of a modulator may result in an increase or decrease in the magnitude of a certain activity compared to the magnitude of the activity in the absence of the modulator. In certain embodiments, a modulator is an inhibitor or antagonist, which decreases the magnitude of one or more activities. In certain embodiments, an inhibitor completely prevents one or more biological activities. In certain embodiments, a modulator is an activator or agonist, which increases the magnitude of at least one activity. In certain embodiments the presence of a modulator results in an activity that does not occur in the absence of the modulator. As used herein, the terms "inhibiting," "reducing," "preventing," or "antagonizing," or any variations of these terms as used herein, refer to a measurable decrease of a biological activity. In some embodiments, the decrease is a 10%, 15%, 20%, 30%, 40%, 50%, 60%, 70%, 80%, 90%, 95%, or 99% reduction in the biological activity relative to a control. As used herein, the terms "stimulating," "increasing," or "agonizing," or any variations of these terms as used herein, refer to a measurable increase of a biological activity. In some embodiments, the increase is a 10%, 15%, 20%, 30%, 40%, 50%, 60%, 70%, 80%, 90%, 95%, or 99% increase in the biological activity relative to a control. A modulator can also be a "silent modulator", wherein the modulator interacts with (e.g., binds to) the target of interest but does not elicit or alter an activity of the target.

Source organism: A "source organism", as that term is used herein, is an organism that naturally contains or produces a polynucleotide, polypeptide, or other compound (e.g., a heterologous nucleic acid) that is to be introduced in accordance with the present invention into a recipient or host cell. In some embodiments, the particular source organism to be selected is not essential to the practice of the present disclosure. Relevant considerations may include, for example, how closely related the potential source and host organisms are in evolution, or how related the source organism is with other source organisms from which sequences of other relevant nucleic acids and/or polypeptides have been selected. Where a plurality of different heterologous nucleic acids are to be introduced into and/or expressed by a host cell, different sequences may be from different source organisms, or from the same source organism. To give but one example, in some cases, individual polypeptides may represent individual subunits of a complex protein activity and/or may be required to work in concert with other polypeptides in order to achieve the goals of the present disclosure. In some embodiments, it will often be desirable for such polypeptides to be from the same source organism, and/or to be sufficiently related to function appropriately when expressed together in a host cell. In some embodiments, such polypeptides may be from different, even unrelated source organisms. It will further be understood that, where a heterologous polypeptide is to be expressed in a host cell, it will often be desirable to utilize nucleic acid sequences encoding the polypeptide that have been adjusted to accommodate codon preferences of the host cell and/or to link the encoding sequences with regulatory elements active in the host cell. In certain embodiments, a gene sequence encoding a given polypeptide is optimized even when such a gene sequence is derived from the host cell itself (and thus is not heterologous). For example, a gene sequence encoding a polypeptide of interest may not be codon optimized for expression in a given host cell even though such a gene sequence is isolated from the host cell strain. In such embodiments, the gene sequence may be further optimized to account for codon preferences of the host cell. Those of ordinary skill in the art will be aware of host cell codon preferences and will be able to employ the methods and reagents described herein and/or known in the art to accommodate them.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Vector: As used herein, "vector" refers to a nucleic acid molecule capable of transporting another nucleic acid to which it has been linked. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

Transient cell expression system: As used herein, "transient cell expression system" refers to an expression system that brings temporary expression of a transformed gene of interest in the desired target cells over a relatively brief time span.

Stable cell expression system: As used herein, "stable cell expression system" regers to an expression system that brings long-term expression of a transformed gene of interest in the desired target cells. This system does not necessarily indicate integration of the gene into the host chromosome and is not passed onto the next generation.

Modulate: As used herein, the term "modulate" typically refers to increase or decrease in the magnitude of a certain activity compared to the magnitude of the activity in the absence of the modulator. As used herein, the terms "inhibiting," "reducing," "preventing," or "antagonizing," or any variations of these terms as used herein, refer to a measurable decrease of a biological activity. In some embodiments, the decrease is a 10%, 15%, 20%, 30%, 40%, 50%, 60%, 70%, 80%, 90%, 95%, or 99% reduction in the biological activity relative to a control. As used herein, the terms "activating", "stimulating," "increasing," or "agonizing," or any variations of these terms as used herein, refer to a measurable increase of a biological activity. In some embodiments, the increase is a 10%, 15%, 20%, 30%, 40%, 50%, 60%, 70%, 80%, 90%, 95%, or 99% increase in the biological activity relative to a control. The term "modulate" can also include "silently modulate", wherein a compound or a modulator interacts with (e.g., binds to) the target of interest but does not elicit or alter an activity of the target.

The term "interact" as used herein is meant to include detectable relationships or association between molecules, such as interaction between a compound and target protein(s) or target protein complex, and interaction between a modulator and target protein(s) or target protein complex. In some embodiments, the term "interact" refers to a situation wherein a compound or a modulator increases or decreases an activity of the target of interest (e.g., target protein(s) or target protein complex). In other embodiments, the term "interact" can also include a situation wherein a compound or a modulator binds to the target of interest but does not elicit or alter an activity of the target.

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., Enantiomers, Racemates and Resolutions (Wiley Interscience, New York, 1981); Wilen, et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972).

[Information on Proteins of the Present Invention]

PRPK is a TP53-regulating kinase registered as NCBI: NP_291028.3. As used herein, naturally occurring or artificially modified mutants of the above-listed PRPK proteins may be also referred to as PPRK so long as they retain the corresponding function.

TPRKB is a TP53RK-binding protein registered as NCBI: NP_057142.1. As used herein, a naturally occurring or artificially modified mutant of the above-listed TPRKB proteins may be also referred to as TPRKB so long as they retain the corresponding function.

PRPK/TPRKB complex: PRPK was first identified as a transcript that is up-regulated in IL-2 activated cytolytic T cells (Abe et al, J. Biol. Chem. 276:44003-44011 (2001)). It has been suggested that PRPK might possess kinase activity and phosphorylate p53 at Ser15 in vitro (Facchin et al (2003) FEBS Letters 549: 63). Kinase activity of recombinant PRPK was not observed unless PRPK was preincubated with cell lysates, suggesting that PRPK may be regulated by other cellular component(s). The physical interaction between PRPK and TPRKB has been demonstrated in vitro (Miyoshi et al, (2003) Biochem. Biophys. Res. Commun. 303:399-405) and there is evidence that PRPK may be activated by Akt (Facchin et al, Cell Mol Life Sci 64:2680-2689 (2007), suggesting that it could be part of an important regulatory pathway relevant to cancer. The human homologs of LAGE3 such as CTAG2 and CTG1B are known as cancer/testis antigens which express specifically in cancer and testis and are a target for cancer immunotherapy (Caballero et al, Cancer Sci (2009) 100, 2014).

"PRPK homolog" or "homolog of PRPK" as used herein may include a homologous protein of PRPK. In some embodiments, examples of "PRPK homolog" include naturally occurring or artificially modified variants of PRPK that have an amino acid sequence having at least 70%, 80%, 90%, 95%, or 99% sequence identity with the sequence of PRPK and possess TP53-regulating kinase activity. "TPRKB homolog" or "homolog of TPRK" as used herein may include a homologous protein of TPRK. In some embodiments, examples of "TPRKB homolog" include naturally occurring or artificially modified variants of TPRKB that have an amino acid sequence having at least 70%, 80%, 90%, 95%, or 99% sequence identity with the sequence of TPRKB and possess p53-related protein kinase-binding activity.

"Homolog of PRPK/TPRKB complex" as used herein may include a complex of a PRPK homolog and a TPRKB homolog, a complex of a PRPK and a TPRKB homolog, and a complex of a PRPK homolog and a TPRKB.

The term "homolog" as used herein refers to trait of homologous protein and/or homologous gene (DNA and/or RNA sequence), which possess functionally and/or sequentially similar protein and/or gene to its original protein and/or gene. The homologous protein and/or gene may be derived from the origin same as or different from that of the original. In some embodiments, the homolog has a sequence having at least 70%, 80%, 90%, 95%, or 99% identity with the sequence of the original protein and/or gene, and the homologous protein encoded in the sequence has a function corresponding to the original one. As used herein, the term "homolog" is no concern with species of protein and/or gene.

[Recombinants of PRPK, TPRKB, and PRPK/TPRKB Complex]

The inventors have discovered that recombinant of PRPK, TPRKB, PRPK/TPRKB complex or homolog thereof is stably expressed at high yield and high purity by using a eukaryotic cell expression system such as baculovirus-insect cell expression system. Cell expression systems other than using eukaryotic cell expression system is not suitable for screening of agents that modulate PRPK, TPRKB, PRPK/TPRKB complex or homolog thereof due to preparing PRPK, TPRKB, PRPK/TPRKB complex or homolog thereof in unstable or functionless condition. A eukaryotic cell expression system enables to provide screening of agents that modulate PRPK, TPRKB, PRPK/TPRKB complex or homolog thereof. In some embodiments, a mammalian cell, an insect cell, and a yeast cell may be used for the eukaryotic cell expression system. Baculovirus-insect cell expression system is preferable.

In some embodiments, polynucleotides encoding the recombinant PRPK, TPRKB, PRPK/TPRKB complex or homolog thereof are incorporated into vectors to construct cell expression vectors, and the expression vectors are then transfected into target cells to prepare transformed cells. Preferably, polynucleotides encoding the recombinant PRPK, TPRKB, PRPK/TPRKB complex or homolog thereof are incorporated into baculovirus vectors to construct baculovirus expression vectors, and the expression vectors are then transfected into insect cells to prepare transformed cells. The recombinants of PRPK, TPRKB, PRPK/TPRKB complex or homolog thereof are obtained at high yield by culturing the transformed cells.

In one embodiment, each proteins composing the PRPK/TPRKB complex or homolog thereof may be expressed in different cell lines, respectively. Alternatively, they may be co-expressed in the same cells. Preferably, the proteins are co-expressed in the same cells. In another embodiment, each proteins composing the PRPK/TPRKB complex or homolog thereof may be expressed in different cells of the same cell line sequentially or in parallel, preferably in parallel.

In one embodiment, each proteins composing the recombinant PRPK/TPRKB complex or homolog thereof may be expressed in different insect cell lines respectively, may be expressed in different cells of the same cell line, or may be co-expressed in the same insect cells. Preferably, the proteins are co-expressed in the same insect cells.

For example, polynucleotides encoding PRPK or TPRKB can be chemically synthesized in accordance with information of the published database, or cDNAs encoding PRPK or TPRKB can be cloned from human cells by any known techniques such as RT-PCR. Homologs of PRPK or TPRKB can be constructed by use of any bioengineering techniques such as site-directed mutagenesis. The Polynucleotides or cDNAs encoding PRPK and/or TPRKB, or a homolog thereof, which may be operably ligated to a tag, such as Flag-tag, Glutathione S-transferase tag or N-terminal six histidine tag (His tag), are cloned into a eukaryotic vector to construct eukaryotic expression vector. The procedures for cloning cDNAs and construction of expression vector are conducted according to a user's manual from the supplier of expression vectors, or as described in Sambrook et al., Molecular Cloning: A Laboratory Manual, Third Edition, Cold Spring Harbor Laboratory Press, New York (2001). The expression vector thus constructed are infected to eukaryotic cells and cultured for a predetermined time period under predetermined culture condition.

In a preferred embodiment, the eukaryotic cell expression system used for expressing the recombinant proteins is baculovirus-insect cell expression system. The exemplified baculovirus-insect cell expression system may be cultured insect cells including a baculovirus vector in which a polynucleotide encoding the recombinant PRPK, TPRKB, PRPK/TPRKB complex or homolog thereof is incorporated. Preferably, examples of the insect cells include Sf9 cells, Sf21 cells, and HiFive, and examples of the baculovirus vectors includes pBacPAK8 and pBacPAK9 (Clontech), pVL1392 (Funakoshi), and 4 pFastBac Dual, 5pDEST8, pDEST10, pDEST20, pFastBac 1, pFastBac HT, pMT/BiP/VS-His, pAc5.1/V5-His, pMT-DEST48, pMT/V5-His-TOPO, pMT/V5-His, pMIB/V5-His, pIB/V5-His-DEST, pIB/His, pIB/V5-His-TOPO, pIB/V5-His, pIZ/V5-His and pIZT/V5-His (Invitrogen). Combination of baculovirus vector pBacPAK9 and insect cell line Sf9 or Sf21 is more preferable.

Because His-PRPK is unstable in Sf9 cells without TPRKB, co-expression of His-PRPK and TPRKB is preferable to obtain the large amount of highly purified PRPK/TPRKB complex. His-PRPK/TPRKB complex can be efficiently purified using His-Trap column (GE Healthcare) because almost all His-PRPK bound to His-Trap column forms the complex with TPRKB and monomeric TPRKB cannot bind to the His-Trap column. Therefore fusing His tag or other tags (e.g. Glutathione S-transferase tag and FLAG tag) to PRPK is preferable to obtain highly purified PRPK/TPRKB complex through an affinity column.

[Identification and/or Characterization of PRPK/TPRKB Complex Modulators]

The present invention also provides a method of identifying an agent that modulates PRPK, TPRKB, PRPK/TPRKB complex, or homolog thereof. In some embodiments, an inventive method screens for modulators of PRPK, TPRKB, PRPK/TPRKB complex, or homolog thereof by identifying agents that bind to PRPK, TPRKB, PRPK/TPRKB complex, or homolog thereof. In some embodiments, an inventive method screens for modulators of PRPK, TPRKB, PRPK/TPRKB complex, or homolog thereof by identifying agents that bind to PRPK, TPRKB, PRPK/TPRKB complex, or homolog thereof with an affinity within the range of less than 1 mM as compared with that of reference agent. In some embodiments, an inventive method screens for modulators of PRPK, TPRKB, PRPK/TPRKB complex, or homolog thereof by identifying agents that treat the symptoms of an oncogenic or cancerous condition. In yet other embodiments, the inventive method identifies modulators of PRPK, TPRKB, PRPK/TPRKB complex, or homolog thereof by identifying agents that modulate expression and/or levels of PRPK, TPRKB, PRPK/TPRKB complex, or homolog thereof.

In some embodiments, the methods of the invention include high throughput screening methods. In certain embodiments, the present invention encompasses agents identified by inventive methods.

It will be understood that all screening methods of the present invention are useful in themselves notwithstanding the fact that effective agents may not be found. The invention provides methods for screening for test agents, not solely methods of finding effective agents.

[Screening]

In some embodiments, screening for modulators of PRPK, TPRKB, PRPK/TPRKB complex, or homolog thereof is employed. In some embodiments, high throughput screening for modulators of PRPK, TPRKB, PRPK/TPRKB complex, or homolog thereof is employed. In some embodiments, such screening identifies substances that bind to PRPK, TPRKB, PRPK/TPRKB complex, or homolog thereof.

In high throughput assays of the invention, it is possible to screen up to several thousand test agents in a single day. Each well of a microtiter plate can be used to run a separate assay against a selected test agent, or, if concentration and/or incubation time effects are to be observed, every 5-10 wells can test a single test agent. Thus, a single standard microtiter plate can assay 96 test agents. If 1536 well plates are used, then a single plate can easily assay from about 100 to about 1500 different test agents. It is possible to assay many plates per day; assay screens for up to about 6,000, 20,000, 50,000, or more than 100,000 different test agents are possible.

For a solid state reaction, the biological target of interest may be bound to the solid state component, directly or indirectly, via covalent and/or non covalent linkage e.g., via a tag. The tag may comprise any of a variety of components. In general, a substance which binds the tag (a tag binder) is fixed to a solid support, and the tagged molecule of interest is attached to the solid support by interaction of the tag and/or the tag binder.

A number of tags and/or tag binders may be used, based upon known molecular interactions well described in the literature. For example, where a tag has a natural binder, for example, biotin, protein A, and/or protein G, it may be used in conjunction with appropriate tag binders (avidin, streptavidin, neutravidin, the Fc region of an immunoglobulin, etc.). Antibodies to molecules with natural binders such as biotin and/or appropriate tag binders are widely available (Sigma Immunochemicals, 1998 catalogue, St. Louis, Mo.).

Similarly, any haptenic and/or antigenic compound may be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are appropriate as tag and/or tag-binder pairs, including but not limited to transferrin, c-kit, viral receptor ligands, cytokine receptors, chemokine receptors, interleukin receptors, immunoglobulin receptors and/or antibodies, the cadherin family, the integrin family, the selectin family, etc. (see, e.g., Pigott et al., The Adhesion Molecule Facts Book I, 1993). Similarly, toxins and/or venoms; viral epitopes; hormones (e.g. opiates, steroids, etc.); intracellular receptors (e.g. which mediate the effects of various small ligands, including steroids, thyroid hormone, retinoids, vitamin D, and/or peptides); drugs; lectins; carbohydrates; nucleic acids (linear and/or cyclic polymer configurations); proteins; phospholipids; and/or antibodies may interact with various cell receptors.

Synthetic polymers, such as polyurethanes, polyesters, polycarbonates, polyureas, polyamides, polyethyleneimines, polyarylene sulfides, polysiloxanes, polyimides, and/or polyacetates may form appropriate tags and/or tag binders. Many other tag/tag binder pairs are useful in assay systems described herein, as would be apparent to one skilled in the art.

Common linkers such as peptides, polyethers, and the like may serve as tags and may include polypeptide sequences, such as poly-Gly sequences of between about 5 and 200 amino acids. Such flexible linkers are known to persons of skill in the art. For example, poly(ethelyne glycol) linkers are available from Shearwater Polymers, Inc. (Huntsville, Ala.). These linkers optionally have amide linkages, sulfhydryl linkages, and/or heterofunctional linkages.

Tag binders are fixed to solid substrates using any of a variety of methods currently available. Solid substrates are commonly derivatized and/or functionalized by exposing all and/or a portion of the substrate to a chemical reagent which fixes a chemical group to the surface which is reactive with a portion of the tag binder. For example, groups which are suitable for attachment to a longer chain portion include amines, hydroxyl, thiol, and/or carboxyl groups. Aminoalkylsilanes and/or hydroxyalkylsilanes may be used to functionalize a variety of surfaces, such as glass surfaces. The construction of such solid phase biopolymer arrays is well described in the literature (see, e.g., Merrifield, 1963, J. Am. Chem. Soc. 85:2149, describing solid phase synthesis of, e.g., peptides; Geysen et al., 1987, J. Immun. Meth. 102:259, describing synthesis of solid phase components on pins; Frank et al., 1988, Tetrahedron 44:6031, describing synthesis of various peptide sequences on cellulose disks); Fodor et al., 1991, Science, 251:767; Sheldon et al., 1993, Clinical Chemistry 39(4):718; and Kozal et al., 1996, Nature Medicine 2:753; all describing arrays of biopolymers fixed to solid substrates). Non-chemical approaches for fixing tag binders to substrates include other common methods, such as heat, cross-linking by UV radiation, and the like.

[In Vitro Assays]

The present invention provides in vitro methods for screening modulators of PRPK, TPRKB, PRPK/TPRKB complex, or homolog thereof. For example, in some embodiments, a method generally comprises steps of: (1) providing a system comprising a PRPK, a TPRKB, a PRPKTPRKB complex, or a homolog thereof; (2) providing a test agent; (3) contacting the test agent with the system; and (4) measuring and/or detecting modulation of PRPK, TPRKB, PRPK/TPRKB complex, or homolog thereof by the test agent.

In general, PRPK, TPRKB PRPK/TPRKB complex, or homolog thereof is provided and brought directly and/or indirectly into contact with a test agent. Then, modulation of PRPK, TPRKB, PRPK/TPRKB complex, or homolog thereof by the test agent is detected and/or measured. Thereafter, suitable agents may be isolated and/or analyzed. For the screening of libraries, the use of high-throughput assays, which are known to the skilled person, are commercially available, and are described herein.

In some embodiments, in vitro assays comprise binding assays. Binding of a candidate substance to a biological target (e.g. PRPK, TPRKB, PRPK/TPRKB complex, and homologs thereof) may, in and of itself, be inhibitory, due to steric, allosteric, and/or charge-charge interactions. The biological target may be free in solution, fixed to a support, and/or expressed in and/or on the surface of a cell. The biological target and/or the test agent may be labeled, thereby permitting detection of binding. The biological target is frequently the labeled species, decreasing the chance that the labeling will interfere with and/or enhance binding. Competitive binding formats may be performed in which one of the test agents is labeled, and one may measure the amount of free label versus bound label to determine the effect on binding.

In some embodiments, binding assays involve exposing a biological target to a test agent and detecting binding between the biological target and the test agent. The binding assay may be conducted in vitro (e.g. in a test tube, comprising substantially only the components mentioned; in cell-free extracts; and/or in substantially purified components). Alternatively or additionally, the assays may be conducted in cyto and/or in vivo (e.g. within a cell, tissue, organ, and/or organism; described in further detail below).

In certain embodiments, a test agent is contacted with a biological target and an effect detected. In one assay, for example, a test agent is contacted with PRPK protein, and binding to PRPK protein is tested. Similar assays may be performed for TPRKB, PRPK/TPRKB complex, or homolog of PRPK, TPRKB or PRPK/TPRKB complex. It will be appreciated that fragments, portions, homologs, variants, and/or derivatives of PRPK, TPRKB and homolog thereof may be employed.

In some embodiments, an assay for identifying agents that bind to a biological target, which is immobilized on a solid support, with a non-immobilized test agent is used to determine whether and/or to what extent the biological target and test agent bind to each other. Alternatively, the test agent may be immobilized and the biological target nonimmobilized. Such assays may be used to identify agents capable of binding to PRPK, TPRKB, PRPK/TPRKB complex or homolog thereof.

In one embodiment, an antibody that recognizes the biological target (e.g. a PRPK antibody) is bound to a solid support (e.g. Protein-A beads). The antibody is contacted with the biological target, which binds to the immobilized antibody. The resulting complex is then brought into contact with the test agent (purified protein, cellular extract, combinatorial library, etc.). If the test agent interacts with the biological target, the test agent will become indirectly immobilized to the solid support. Presence of the test agent on the solid support can be assayed by any standard technique known in the art (including, but not limited to, western blotting). This type of assay is known in the art as an "immunoprecipitation" assay.

In one embodiment, a biological target (e.g., PRPK, TPRKB, PRPK/TPRKB complex and homologs thereof) is immobilized on beads, such as agarose beads. In certain embodiments, PRPK, TPRKB, homolog thereof, and/or a characteristic portion thereof is expressed as a GST-fusion protein in bacteria, yeast, insect, and/or higher eukaryotic cell line and/or purified from crude cell extracts using glutathione-agarose beads. As a control, binding of the test agent, which is not a GST-fusion protein, to the immobilized biological target is determined in the absence of biological target. The binding of the test agent to the immobilized biological target is then determined. This type of assay is known in the art as a "GST pulldown" assay. Alternatively or additionally, the test agent may be immobilized and the biological target non-immobilized.

It is possible to perform this type of assay using different affinity purification systems for immobilizing one of the components, for example Ni-NTA agarose- and/or histidine-tagged components.

Binding of a biological target to a test agent may be determined by a variety of methods well-known in the art. For example, a non-immobilized component may be labeled (with for example, a radioactive label, an epitope tag, and/or an enzyme-antibody conjugate). Alternatively, binding may be determined by immunological detection techniques. For example, a reaction mixture may be Western blotted and the blot probed with an antibody that detects the non-immobilized component. Alternatively or additionally, enzyme linked immunosorbent assay (ELISA) may be utilized to assay for binding.

[Methods of Use]

The present invention provides methods of treating a disease, condition, or disorder associated with PRPK, TPRKB, PRPK/TPRKB complex, or homolog thereof. In some embodiments, the present invention provides methods of treating a disease, condition, or disorder associated with cell proliferation. In certain embodiments, such methods involve modulating PRPK, TPRKB, PRPK/TPRKB complex, or homolog thereof. In certain embodiments, such methods involve activating PRPK, TPRKB homolog thereof, or PRPK/TPRKB complex. In certain embodiments, such methods involve inhibiting PRPK, TPRKB, PRPK/TPRKB complex, or homolog thereof.

In some embodiments, the present invention provides methods of inhibiting cell proliferation comprising contacting a cell with an agent that modulates PRPK/TPRKB complex and/or any subunit or component thereof, and optionally further comprising a step of detecting a decrease in cell proliferation compared to a control.

[Exemplification]

The representative Examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following Examples contain important additional information, exemplification and guidance that can be adapted to the practice of this invention in its various embodiments and the equivalents thereof. It will be appreciated, however, that these examples do not limit the invention. Variations of the invention, now known and/or further developed, are considered to fall within the scope of the present invention as described herein and as hereinafter claimed.

General Cell Culture. Cell lines JeKo-1 was obtained from ATCC and maintained by vendor-specified media requirements at 37° C. in 5% $CO_2$ incubators. Cryopreserved PBMCs were obtained from Astarte Biologics and thawed and maintained by vendor-specified media requirements.

Reference Example 1

Synthesis of Pomalidomide-Based Affinity Agent

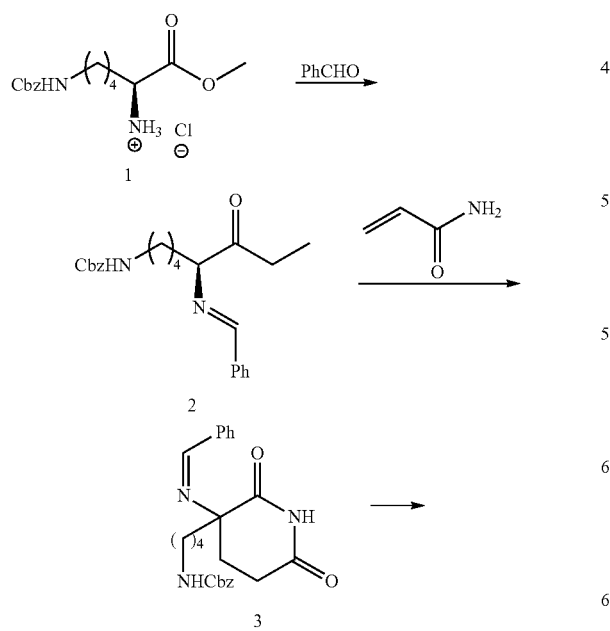

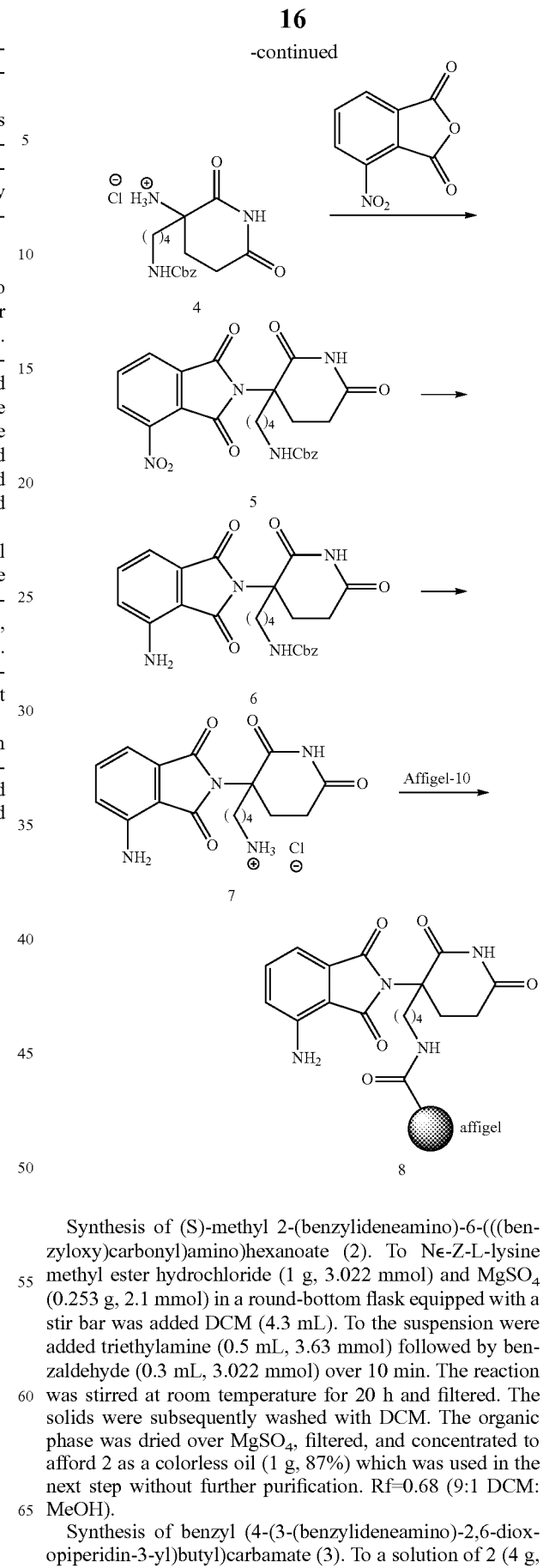

Synthesis of (S)-methyl 2-(benzylideneamino)-6-(((benzyloxy)carbonyl)amino)hexanoate (2). To Nε-Z-L-lysine methyl ester hydrochloride (1 g, 3.022 mmol) and $MgSO_4$ (0.253 g, 2.1 mmol) in a round-bottom flask equipped with a stir bar was added DCM (4.3 mL). To the suspension were added triethylamine (0.5 mL, 3.63 mmol) followed by benzaldehyde (0.3 mL, 3.022 mmol) over 10 min. The reaction was stirred at room temperature for 20 h and filtered. The solids were subsequently washed with DCM. The organic phase was dried over $MgSO_4$, filtered, and concentrated to afford 2 as a colorless oil (1 g, 87%) which was used in the next step without further purification. Rf=0.68 (9:1 DCM: MeOH).

Synthesis of benzyl (4-(3-(benzylideneamino)-2,6-dioxopiperidin-3-yl)butyl)carbamate (3). To a solution of 2 (4 g, 10.4 mmol) and acrylamide (1.11 g, 15.7 mmol) in THF (40 mL) was added portionwise potassium tert-butoxide (1.23 g, 11.0 mmol) over a period of 15 min at 0° C. After 3.5 h, the mixture was quenched with aqueous NH$_4$Cl and extracted into EtOAc. The organic layer was dried over MgSO$_4$, filtered, and concentrated to afford 3 (3.6 g, 82%) without further purification. Rf=0.33 (95:5 DCM:MeOH).

Synthesis of benzyl (4-(3-amino-2,6-dioxopiperidin-3-yl)butyl)carbamate hydrochloride (4). To a solution of 3 (3.6 g, 8.54 mmol) in THF (21 mL) was added portionwise aqueous 4 M HCl at 0° C. The mixture was allowed to reach room temperature and stirred over 5 h. A white precipitated that formed during the reaction was filtered and washed with THF. Two recrystallizations afforded 4 (2.88 g, 91.2%) as a white solid. $^1$H NMR (400 MHz, DMSO) δ 11.30 (s, 1H), 8.62 (br s, 3H), 7.46-7.15 (m, 5H), 4.97 (m, 2H), 3.59 (m, 2H), 2.98 (m, 2H), 2.76 (m, 1H), 2.58 (m, 1H), 2.24-1.97 (m, 2H), 1.85 (m, 2H), 1.74 (m, 1H), 1.21 (m, 1H).

Synthesis of benzyl (4-(3-(4-nitro-1,3-dioxoisoindolin-2-yl)-2,6-dioxopiperidin-3-yl)butyl)carbamate (5). To a mixture of 4 (0.326 g, 0.881 mmol), 3-nitrophthalic anhydride (0.211 g, 1.093 mmol) and sodium acetate (0.097 g, 1.181 mmol) was added acetic acid (4.0 mL) and the resulting mixture was stirred overnight at 130° C. After 20 h, the mixture was carefully neutralized with sodium bicarbonate and extracted into DCM. The organic layer was dried over MgSO$_4$, filtered, and concentrated. Purification by flash chromatography (95:5 DCM:MeOH) afforded 5 (0.241 g, 54%) as a white solid.

Synthesis of benzyl (4-(3-(4-amino-1,3-dioxoisoindolin-2-yl)-2,6-dioxopiperidin-3-yl)butyl)carbamate (6). To a suspension of 5 (0.24 g, 0.472 mmol) in ethanol (15 mL) was added Raney Nickel (W.R. Grace and Co. Raney® 4200, slurry, in H2O) under argon. The mixture was subsequently saturated with hydrogen using a hydrogen balloon. After 1.5 h, the mixture was flushed with argon, filtered using EtOH and concentrated. Purification by flash chromatography (95:5 DCM:MeOH) afforded 6 (0.112 mg, 49%) as a bright yellow solid. Rf=0.38 (95:5 DCM:MeOH). $^1$H NMR (400 MHz, DMSO) δ 10.97 (s, 1H), 9.09 (s, 1H), 9.04 (s, 1H), 7.71-7.52 (m, 2H), 7.49-7.18 (m, 5H), 7.10 (m, 1H), 5.07-4.85 (m, 2H), 2.96 (m, 2H), 2.55 (m, 2H), 2.44 (m, 1H), 2.22 (m, 2H), 2.02 (m, 1H), 1.40 (m, 2H), 1.22 (m, 2H). MS (ESI) m/z calcd for C$_{25}$H$_{27}$N$_4$O$_6$ [M+H]$_+$ 479.5. found 479.9.

Synthesis of 4-amino-2-(3-(4-aminobutyl)-2,6-dioxopiperidin-3-yl)isoindoline-1,3-dione hydrochloride (7). To a solution of 6 (0.111 g, 0.232 mmol) in 2% HCl in ethanol (60 mL) was added palladium on activated charcoal (0.025 g) under an atmosphere of argon. The mixture was subsequently saturated with hydrogen using a hydrogen balloon. After 4 h, the mixture was flushed with argon, filtered using ethanol and methanol. Preparative HPLC afforded 7 (0.055 g, 69%) as a bright yellow solid. $^1$H NMR (400 MHz, DMSO) δ 8.31 (s, 1H), 7.52-7.34 (m, 1H), 6.94 (m, 2H), 6.53 (br s, 2H), 2.74 (t, J=7.4 Hz, 2H), 2.65 (m, 1H), 2.63-2.56 (m, 1H), 2.54 (m, 1H), 2.44 (m, 1H), 2.31 (m, 1H), 2.21 (m, 1H), 2.02 (m, 1H), 1.52 (m, 1H), 1.48-1.38 (m, 1H), 1.26 (m, 2H). MS (ESI) m/z calcd for C17H21N4O4 [M+H]$^+$345.4. found 345.7.

Synthesis of 8 (pomalidomide-based affinity reagent). About 2 mL of a suspension of affigel-10 (15 μmol/mL of gel, 50% slurry) in isopropanol was transferred to a conical tube and centrifuged to a settled volume of 1.04 mL. The isopropanol was removed and the affigel-10 was washed with DMSO (3×5 mL). A DMSO (2.2 mL) solution of 7 (0.002 g, 0.00525 mmol) and triethylamine (0.007 mL, 0.0525 mmol) was subsequently added and the resulting mixture was sealed and tumbled on a rotator at room temperature. After 16 h, the conical tube was spun down and the DMSO supernatant was tested for the presence of 7 by LC-MS. 7 was not observed and therefore to the mixture was added triethylamine (0.015 mL, 0.105 mmol) and ethanolamine (0.006 mL, 0.10503 mmol) and the resulting mixture was tumbled on a rotator at room temperature. After 20 h, SS-0007896 was spun down, the solvent was removed, and the resin was washed with DMSO (3×5 mL) and isopropanol (3×5 mL) and stored in isopropanol at −20° C.

Referential Example 2

Target Discovery by Standard Small Molecule Affinity Chromatography

Cell lysates were prepared from 2×108 Jeko-1, Jurkat, or HS-Sultan cells or 5×10$^7$ HeLa S3 cells per pulldown sample by lysis in 2 mL Buffer B (50 mM HEPES pH 7.5, 5% glycerol, 1.5 mM MgCl$_2$, 150 mM NaCl, 1 mM Na$_3$VO$_4$, 25 mM NaF, 0.4% Nonidet P-40, 1 mM DTT, and 1 Complete Mini EDTA-free protease inhibitor tablet per 10-25 mL Buffer B). Lysates were incubated on ice for 30 min, followed by 2× freeze-thaw using liquid N2 and 37° C. water bath in polypropylene tubes. Samples were centrifuged at 1800 rpm for 5 min at 4° C. Supernatants were ultracentrifuged at 55,000 rpm for 1 hr at 4° C. Supernatants were collected and pre-cleared with 10 control affigel reagent (affigelethanolamine or affigel-PEG linker) by incubation on a rotator for 30 min at 4° C. Precleared lysates were transferred to Mobicol 1 mL columns with 90 μm pore size frit on ice and centrifuged at 0.1 rcf for 10 sec to separate affigel beads from lysates. Incubations with pre-cleared lysates and excess pomalidomide were performed at a 20-fold excess competitor concentration (500 μM final concentration) on a rotator for 30 min at 4° C. Subsequently, 10 μL control or pomalidomide-based affigel reagents were added to each sample and pulldowns were performed for 1 hr at 4° C. Lysates and affigel reagents were transferred to Mobicol 1 mL columns with 90 μm pore size frit and affigel beads were washed 3× with 800 μL Buffer B and 2× with 800 μL Buffer A (Buffer B not including 0.4% Nonidet P-40). Columns were centrifuged for 30 sec at 0.1 rcf to remove any remaining wash buffer and then closed with lower plug. Columns were placed in 1.5 mL Low-binding Eppendorf tubes and heated at 50° C. for 30 min in 40 μL 2×SDS sample buffer with 10 mM DTT to elute bound proteins from affigel reagents. Columns were then opened and eluents were collected in the low-binding Eppendorf tubes by 15 sec centrifugation at 1600 rpm. Samples were applied and resolved on 4-12% SDS-PAGE gels followed by silver staining (SilverQuest Kit, Invitrogen, Carlsbad, Calif.). Bands which were competed by excess pomalidomide competitor but not by DMSO were excised and identified by LC/MS/MS analysis at the Beth Israel Deaconess Medical Center Mass Spectrometry Core Facility (Boston, Mass.), (See FIG. 1.)

Example 1

Complex of Human PRPK and TPRKB Proteins in Sf9 Cells

Human PRPK (NM_033550.3) cDNA was cloned into pBacPAK9 vectors (Clontech) with or without the Glutathione S-transferase tag (GST-tag) with TEV protease cleavage site, the 6× histidine tag (His-tag) with TEV protease cleavage site, or FLAG-tag. Human TPRKB (NM_016058.2) cDNA was also cloned into pBacPAK9 vectors with or without GST-tag with TEV protease cleavage site, His-tag with TEV protease cleavage site, His-tag, or FLAG-tag. Recombinant baculoviruses encoding GST-tag fused PRPK (GST-PRPK), His-tag fused PRPK (His-PRPK), FLAG-tag fused PRPK (PRPK-FLAG), PRPK, GST-tag fused TPRKB (GST-TPRKB), His-tag fused TPRKB (His-TPRKB and TPRKB-His), FLAG-tag fused TPRKB (TPRKB-FLAG), and TPRKB were constructed using Bac-PAK Baculovirus Expression system (Clontech) according to Clontech's User Manual.

The recombinant baculoviruses encoding GST-PRPK and His-TPRKB or those encoding GST-PRPK and TPRKB-His were co-infected to Sf9 insect cells (Invitrogen) with the following ratio; 5:1, 2:1, 1:1, 1:2. The infected Sf9 cells were cultured in Grace's insect medium (Invitrogen) containing 0.1% Pluronic ion (Invitrogen), 1× Kanamycin Sulfate (Invitrogen) and 10% FCS at 27° C. for 3 days or 4 days. The cells were harvested and lysed by the sonication in the Lysis buffer (50 mM HEPES pH 7.5, 200 mM Li2SO4, 5% glycerol, 0.5% CHAPS, 1× complete EDTA-free (Roche), 10 mM 2-mercaptoethanol). After the centrifuge (15 k rpm×30 min at 4° C.), the supernatants were collected as the crude lysates. Glutathione-sepharose 4B beads (GE Healthcare) was added to the crude lysates and incubated for 1 hour at 4° C. with rotation. Binding proteins were eluted by the addition of 1× sample buffer (45 mM Tris-Cl, pH6.8, 715 mM 2-mercaptoethanol, 1.5% SDS, 3% glycerol, 0.00375% Bromophenol Blue). Crude lysates and binding proteins were analyzed by SDS-PAGE and western blot analysis using anti-GST antibody (GE Healthcare) or anti-His-tag antibody (Sigma).

Figure 2:
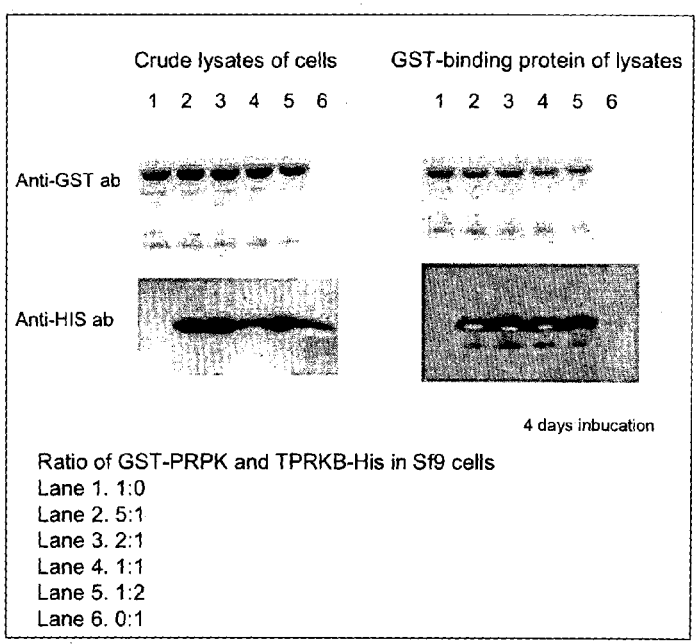
FIG. 2. Recombinant human PRPK and TPRKB proteins in Sf9 cells.

After incubation for 3 days as well as 4 days, both PRPK and TPRKB proteins were expressed in Sf9 cells. The results of GST-pull down experiment showed that GST-PRPK and His-TPRKB/TPRKB-His proteins formed complex successfully in insect cells (See FIG. 2).

Example 2

Purification of Complex of Human PRPK and TPRKB Proteins

Figure 3:
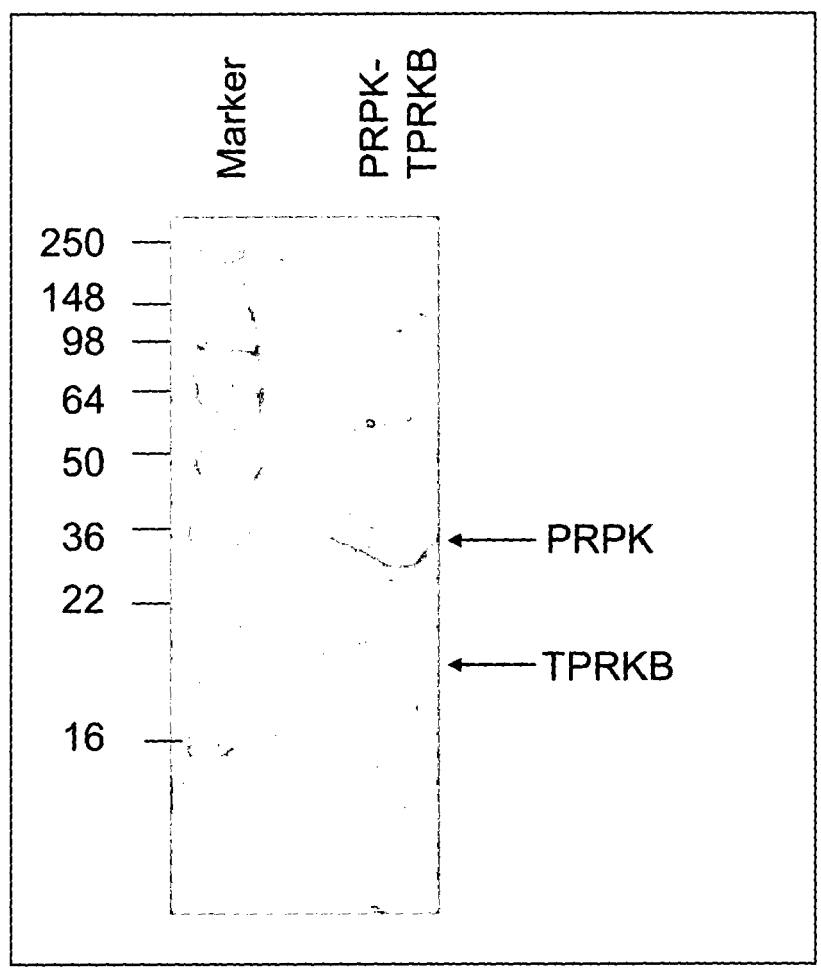
FIG. 3. Recombinant human PRPK and TPRKB proteins purified from Sf9 cells.

Recombinant baculoviruses encoding His-PRPK and TPRKB were produced by BacPAK Baculovirus Expressing system as shown in the previous section. For complex formation of His-PRPK with TPRKB in Sf9 cells, Sf9 cells were co-infected with the recombinant baculoviruses encoding His-PRPK and TPRKB and then cultured in Grace's insect medium containing 0.1% Pluronic ion, 1× Kanamycin Sulfate and 10% FCS at 27° C. for 3 days. After the 3-day culture, the infected Sf9 cells were harvested and whole cell lysates were prepared by sonication of the cells in the lysis buffer (50 mM HEPES pH 7.5, 200 mM Li2SO4, 5% glycerol, 0.5% CHAPS, 1× complete EDTA-free (Roche), 10 mM 2-mercaptoethanol) and then centrifuged at 40000×g for 30 min. The supernatant was applied on His-affinity columns, HisTrap (GE Healthcare) and TALON (Clontech) to obtain fractions containing the complex of His-PRPK and TPRKB. These fractions were incubated with His-tagged TEV protease (Invitrogen) at 4° C. over-night and then applied on TALON column to remove the protease. The flow through fraction of the TALON column was applied on a cation-exchange column, MonoS (GE Healthcare) to obtain fractions containing the complex of PRPK and TPRKB. During the course of the purification, PRPK and TPRKB proteins were traced by SDS-PAGE and followed by coomassie brilliant blue staining. Protein concentration was determined using Quick Start Bradford Dye Reagent (BIO-RAD) and the level of purity was analyzed using 12.5% SDS-PAGE followed by coomassie brilliant blue staining (See FIG. 3). Total 72 mg purified protein were obtained from 6 L of Sf9 cell culture.

Example 3

Increased Expression in Baculovirus Expression System

The yields of the PRPK/TPRKB complex expressed in different eukaryotic cells were determined, in which PRPK-FLAG and TPRKB-FLAG were co-expressed in eukaryotic cell system using HEK293F (human embryonic kidney derived cell line, Invitrogen) with mammalian expression vectors or His-PRPK and TPRKB were co-expressed in Sf9 insect cell line with baculovirus-expression system to determine the expression level. The amount of purified protein was determined using BCA Protein Assay Kit (Thermo Scientific) or Quick Start Bradford Dye Reagent (BIO-RAD). The yields of the PRPK/TPRKB complex were 50-70 µg protein/200 mL culture in HEK293F, and more than 10 mg/L culture in insect cells. Therefore baculovirus expression system is 30 times more efficient than mammalian expression system.

Example 4

Biotinylation of Pomalidomide Derivatives

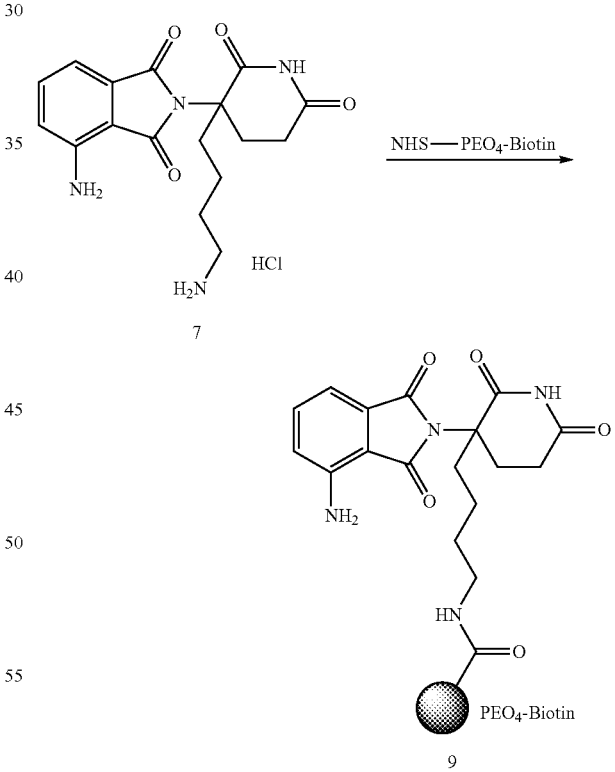

To the solution of pomalidomide-based affinity reagent (7) dissolved in methanol at a concentration of 1 mg/ml, a 0.85-fold molar excess of NHS-PEO$_4$-Biotin (Pierce Biotechnology) dissolved in water (34 mM) was added. The reaction mixture was incubated at room temperature for 4 hours with continuous shaking. For negative control experiments, the same reaction was executed using ethanolamine as a substitute for (7). Progression of the reactions was confirmed by the methods of thin layer chromatography and liquid chromatography-mass spectrometry.

Figure 4:
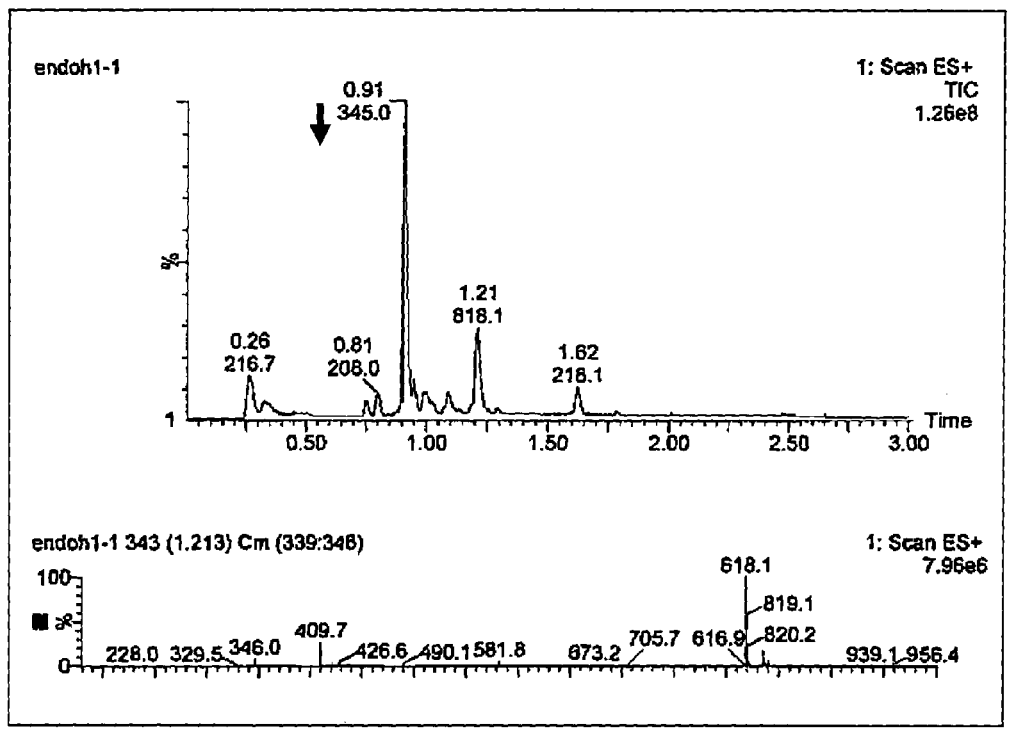
FIG. 4. Synthesis of biotinyl pomalidomide derivative confirmed by LC/MS analysis.

Biotinyl pomalidomide derivative (9) with 618.1 molecular weight was detected by LC/MS at 1.21 min (See FIG. 4).

Example 5

Surface Plasmon Resonance Analysis

Figure 5:
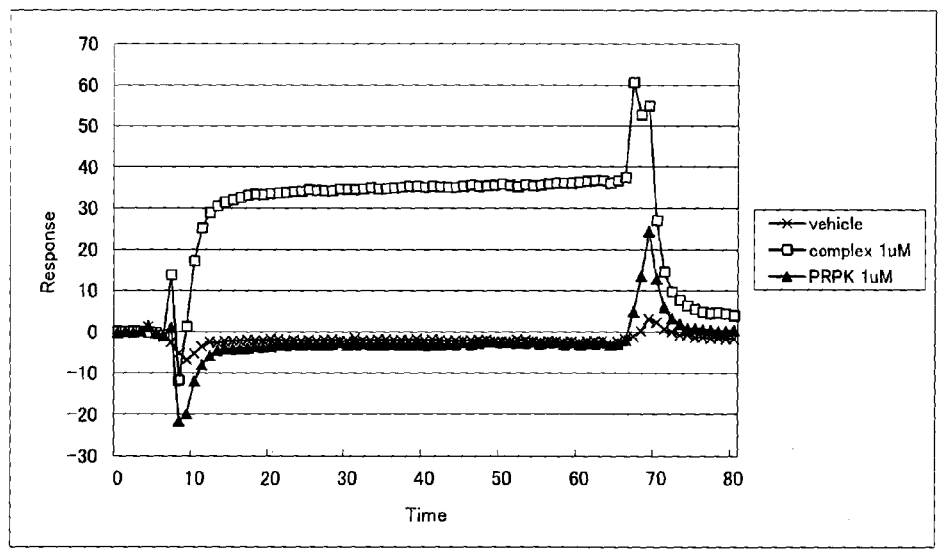
FIG. 5. Surface plasmon resonance analysis of PRPK/TPRKB complex.

Real time analysis of the interaction between pomalidomide and the PRPK/TPRKB complex was performed with a Biacore 2000 system (GE Healthcare) using a flow rate of 5 µl/min. A streptavidin-coated sensor chip (GE Healthcare) was activated using 1 M NaCl and 50 mM NaOH for 1 min two times. Biotinylated pomalidomide (9) dissolved in Biacore HBS-EP buffer {0.01 M HEPES buffer (pH 7.4), 0.15 M NaCl, with 0.005% Surfactant P20} was perfused for 4 min. For blocking the non-reacted streptavidin, biothinylated ethanolamine was perfused for 10 min two times. Successful immobilization was confirmed by the observation of an appropriate RU response. The PRPK/TPRKB complex was perfused and allowed to interact with immobilized pomalidomide for 1 min. The interaction between immobilized free-pomalidomide derivative and the PRPK/TPRKB complex was observed. The sensor chip was perfused with HBS-EP buffer for 1 min for dissociation and was regenerated by injecting 0.5% (v/v) DMSO and 0.01% SDS in HBS-EP buffer for 2 min. (See FIG. 5.)

EQUIVALENTS AND SCOPE

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. For example, it is to be understood that any of the compositions of the invention can be used for inhibiting the formation, progression, and/or recurrence of adhesions at any of the locations, and/or due to any of the causes discussed herein or known in the art. It is also to be understood that any of the compositions made according to the methods for preparing compositions disclosed herein can be used for inhibiting the formation, progression, and/or recurrence of adhesions at any of the locations, and/or due to any of the causes discussed herein or known in the art. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention (e.g., any derivative, any molecular weight range, any cross-linking agent, any type of bond hydrogel precursors, any class of biologically active agent or specific agent, any material composition, any route or location of administration, any purpose for which a composition is administered, etc.), can be excluded from any one or more claims. For purposes of brevity, all of the embodiments in which one or more elements, features, purposes, or aspects are excluded are not set forth explicitly herein.

The invention claimed is:

1. A method of preparing a recombinant complex of PRPK and TPRKB, the method comprising:
   expressing, in an insect cell, a baculovirus vector comprising a polynucleotide encoding PRPK and a polynucleotide encoding TPRKB so that the complex of PRPK and TPRKB is formed; or
   co-expressing, in an insect cell, at least two baculovirus vectors, wherein one baculovirus comprises the polynucleotide encoding PRPK and a second baculovirus comprises the polynucleotide encoding TPRKB so that the complex of PRPK and TPRKB is formed.

2. The method according to claim 1, further comprising purifying the complex of PRPK and TPRKB.

3. The method according to claim 1, wherein the insect cell is an Sf9 cell or an Sf21 cell, and the baculovirus vector is pBacPAK9.

4. The method according to claim 1, comprising co-expressing, in an insect cell, at least two baculovirus vectors, wherein one baculovirus comprises the polynucleotide encoding PRPK and a second baculovirus comprises the polynucleotide encoding TPRKB so that the complex of PRPK and TPRKB is formed.

5. The method according to claim 4, further comprising purifying the complex of PRPK and TPRKB.

6. The method according to claim 4, wherein the insect cell is an Sf9 cell or an Sf21 cell, and the baculovirus vector is pBacPAK9.

\* \* \* \* \*